United States Patent
Li et al.

(10) Patent No.: US 10,324,054 B2
(45) Date of Patent: Jun. 18, 2019

(54) METHOD OF MANUFACTURING SENSOR DEVICE

(71) Applicant: Industrial Technology Research Institute, Hsinchu (TW)

(72) Inventors: Sih-Han Li, New Taipei (TW); Chih-Sheng Lin, Tainan (TW); Kuan-Wei Chen, Taichung (TW); Erh-Hao Chen, Changhua County (TW); Shyh-Shyuan Sheu, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 16/178,599

(22) Filed: Nov. 2, 2018

(65) Prior Publication Data

US 2019/0079039 A1    Mar. 14, 2019

Related U.S. Application Data

(62) Division of application No. 14/961,906, filed on Dec. 8, 2015, now Pat. No. 10,156,535.

(30) Foreign Application Priority Data

Oct. 30, 2015 (TW) .............................. 104135766 A

(51) Int. Cl.
*G01N 27/12* (2006.01)
(52) U.S. Cl.
CPC ......... *G01N 27/127* (2013.01); *G01N 27/121* (2013.01)

(58) Field of Classification Search
CPC .. G01N 27/121; G01N 27/125; G01N 27/127; G01N 27/30; G01N 27/403; G01N 27/407; G01N 27/4073; G01N 27/4075; G01N 27/4146; G01N 33/0009; G01N 33/0027; G01N 33/0031; G01N 33/0032
USPC ................... 73/25.05, 31.05, 335.02, 335.05
See application file for complete search history.

(56) References Cited

U.S. PATENT DOCUMENTS

| | | | | |
|---|---|---|---|---|
| 2008/0210987 A1* | 9/2008 | Bondavalli | ............ | B82Y 15/00 257/253 |
| 2008/0277746 A1* | 11/2008 | Hsu | ...................... | B81C 1/00095 257/414 |
| 2012/0302454 A1* | 11/2012 | Esfandyarpour | ....... | C40B 60/12 506/9 |
| 2013/0311108 A1* | 11/2013 | Stetter | .................... | G01N 27/00 702/22 |

* cited by examiner

*Primary Examiner* — Benjamin R Schmitt
(74) *Attorney, Agent, or Firm* — JCIPRNET

(57) ABSTRACT

A method of manufacturing a sensor device is provided. In the method, sensing electrodes are formed on a substrate, a sensing material layer is formed on the sensing electrodes. The sensing material layer is etched to form a first nanowire sensing region, a second nanowire sensing region and a third nanowire sensing region respectively between every two sensing electrodes of the sensing electrodes. A dielectric layer is formed to cover the first nanowire sensing region, the second nanowire sensing region and the third nanowire sensing region, and the first nanowire sensing region and the third nanowire sensing region are exposed.

10 Claims, 10 Drawing Sheets

METHOD OF MANUFACTURING SENSOR DEVICE

CROSS-REFERENCE TO RELATED APPLICATION

This application is a divisional application of and claims the priority benefit of U.S. patent application Ser. No. 14/961,906, filed on Dec. 8, 2015, now allowed. The prior application Ser. No. 14/961,906 claims the priority benefit of Taiwan application serial no. 104135766, filed on Oct. 30, 2015. The entirety of each of the above-mentioned patent applications is hereby incorporated by reference herein and made a part of this specification.

TECHNICAL FIELD

The disclosure relates a method of manufacturing a sensor device that senses gas, humidity and temperature.

BACKGROUND

The three important layers in the Internet of Things (IoT) are the perception layer, the internet layer and the application layer, and the most important component in the perception layer is the sensor. Therefore, as the technology IoT continues to develop, the demands for sensors increase correspondingly. Currently, sensors that are miniature, low in power consumption and highly sensitive are the most demanding in applications, especially for wearable or mobile phone devices.

Presently, the most fundamentally and customarily used sensors are gas, temperature, and humidity sensors, wherein in most gas sensors, a temperature sensor and a humidity sensor are integrated on an extra system board for performing calibrations under the different ambient conditions to provide a better accuracy. Alternatively speaking, most gas sensors are arranged with temperature and humidity sensors. However, for wearable or mobile phone devices, the space for accommodating sensors is very limited; hence, to miniaturize and integrate sensors of various functions in a same fabrication process has been actively pursued by the relevant industries.

SUMMARY

An exemplary embodiment of the disclosure relates to a method for manufacturing a sensor device. The method includes forming a plurality of sensing electrodes on a substrate, followed by forming a sensing material layer on the sensing electrodes and then etching the sensing material layer to form a first nanowire sensing region, a second nanowire sensing region and a third nanowire sensing region respectively between every two sensing electrodes. A dielectric layer is further formed to cover the first nanowire sensing region, the second nanowire sensing region and the third nanowire sensing region, and the first nanowire sensing region and the third nanowire sensing region are subsequently exposed.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

FIGS. 4A, 4B-1, 4B-2, 4C, 4D-1, 4D-2 and 4E are schematic views exemplarily illustrating respective steps of a method for manufacturing a sensor device according to a fourth embodiment of the disclosure.

FIGS. 5A-1, 5A-2, 5B-1, 5B-2, 5C-1, 5C-2, 5D-1 and 5D-2 are schematic views exemplarily illustrating variations of the fourth embodiment of the disclosure on the method for manufacturing a sensor device.

DETAILED DESCRIPTION OF DISCLOSED EMBODIMENTS

Figure 1:
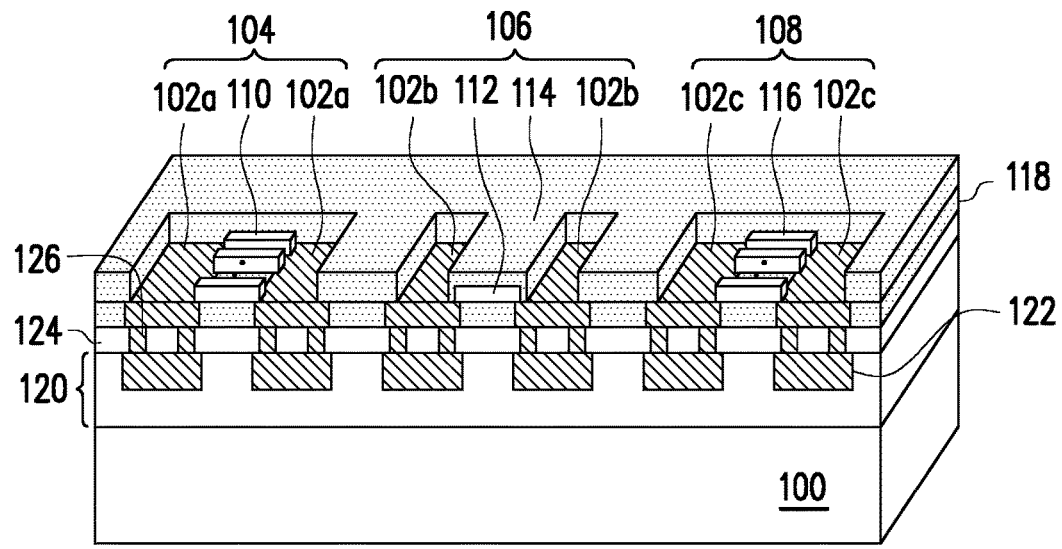
FIG. 1 is a stereoscopic schematic view exemplarily illustrating a sensor device according to a first embodiment of the disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

FIG. 1 is a stereoscopic schematic view exemplarily illustrating a sensor device according to a first embodiment of the disclosure.

In the embodiment as shown in FIG. 1, a sensor device includes a substrate 100, a plurality of sensing electrodes 102a-102c, a humidity nanowire sensor 104, a temperature nanowire sensor 106, and a gas nanowire sensor 108. The substrate 100 may be, for example, a silicon chip or other types of appropriate substrate. The sensing electrodes 102a-102c are formed on the substrate 100 and the size of each sensing electrode 102a-102c is 50 µm×50 µm or more to facilitate sensing. The material of the above sensing electrodes 102a-102c may be selected from, for example, at least one pure metal of or an alloy of platinum (Pt), titanium (Ti), tungsten (W), copper (Cu), aluminum (Al), but excluding pure copper. If the material of the sensing electrodes 102a-102c is, for example, an alloy, the material of the sensing electrodes 102a-102c may include CuAl, TiCu, TiW, TiCuAl, etc. The humidity nanowire sensor 104, the temperature nanowire sensor 106, and the gas nanowire sensor 108 are also configured on the substrate 100. In the embodiment, the humidity nanowire sensor 104 includes an exposed first nanowire sensing region 110 and two sensing electrodes 102a that are respectively connected with two ends of the first nanowire sensing region 110. The temperature nanowire sensor 106 includes a second nanowire sensing region 112, two sensing electrodes 102b that are respectively connected with two ends of the second nanowire sensing region 112 and a dielectric layer 114 covering the second nanowire sensing region 112. The gas nanowire sensor 108 includes an exposed third nanowire sensing region 116 and two sensing electrodes 102c that are respectively connected with two ends of the third nanowire sensing region 116.

From the perspectives of reducing the manufacturing cost, the above first, second and third nanowire sensing regions 110, 112 and 116 are formed with a same sensing material layer; further, the size of the first nanowire sensing region 110 will have different sensitives for different humidity levels, the size of the second nanowire sensing region 112 will also affect its sensitivity on temperatures, and the different nanowire diameters of the third nanowire sensing region 116 will have different sensitivities for different gases. Therefore, the sizes (diameters) of the nanowires of the first, second and third nanowire sensing regions 110, 112 and 116 may vary based on the designs, for example, between 100 nm and 1000 nm; in another embodiment, the sizes (diameters) of the nanowires may be between 50 nm and 350 nm. Further, the nanowires of the first, second and third nanowire sensing regions 110, 112 and 116 may have the same or different diameters, but the disclosure is not limited thereto. The above first, second and third nanowire sensing regions 110, 112 and 116 may form with different sensing material layers. The material used in forming the sensing material layers for the above first, second and third nanowire sensing regions 110, 112 and 116 may include tin oxide ($SnO_2$), titanium oxide ($TiO_2$), zinc oxide (ZnO) or polysilicon (poly Si). In some embodiments, a hydrophilic material, such as titanium oxide, tin oxide, etc., is used. The dielectric layer 114 that covers the second nanowire sensing region 112 may also be covering other parts on the substrate 100 while exposing the sensing electrodes 102 a-102c. The material of the dielectric layer 114 may include silicon oxide ($SiO_2$), silicon nitride (SiN) or other appropriate materials. Although the second nanowire region 112 is covered by the dielectric layer 114 and a cross-section thereof is exposed in the Figures, one can easily realize that the second nanowire sensing region 112, which is similar to the first nanowire sensing region 110 or the third nanowire sensing region 116, is formed with a plurality of nanowires. The first and third nanowire sensing regions 110, 116 in FIG. 1 are exemplified to have three nanowires, whereas the black dots in between signify that the number of the nanowires can be increased based on the designs.

Figure 2:
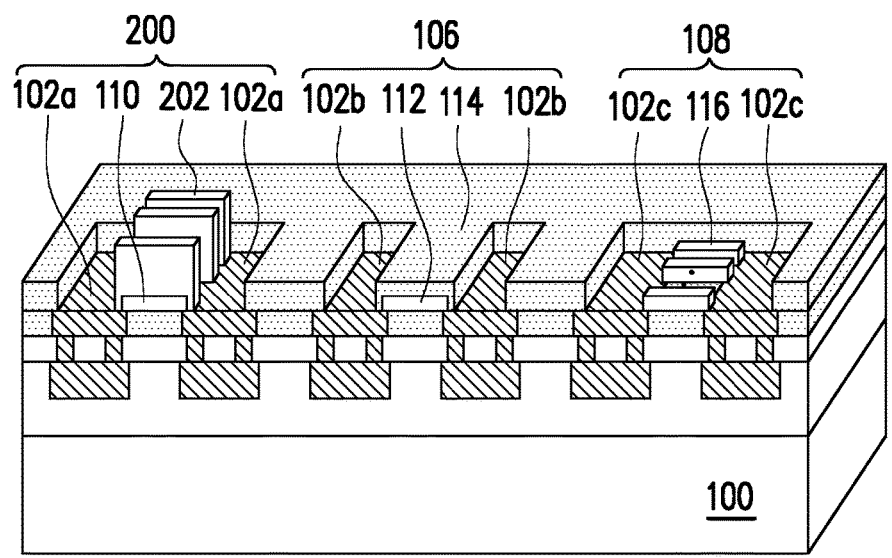
FIG. 2 is a stereoscopic schematic view exemplarily illustrating a sensor device according to a second embodiment of the disclosure.

FIG. 2 is a stereoscopic schematic view exemplarily illustrating a sensor device according to a second embodiment of the disclosure, wherein the same reference numbers are used to represent the same or similar structures as shown in FIG. 1.

Referring to FIG. 2, a difference between the first embodiment and the second embodiment lies in that the humidity nanowire sensor 200, in addition to the first nanowire sensing region 110 and the sensing electrodes 102a, also includes a hydrophilic material layer 202 covering the first nanowire sensing region 110, wherein the hydrophilic material layer may be an ALD layer deposited by the atomic layer deposition (ALD) technique and a material of the hydrophilic material layer 202 may include, but is not limited to, aluminum oxide ($Al_2O_3$), titanium oxide ($TiO_2$), tin oxide ($SnO_2$), Zinc chromate ($ZnCr_2O_4$) or magnesium chromate ($MgCr_2O_4$). Since the first nanowire sensing region 110 is covered by the hydrophilic material layer 202, humidity adsorption is increased to thereby enhance the sensitivity of humidity sensing, even when the nanowire of the first nanowire sensing region 110 is not formed with a hydrophilic material.

Figure 3:
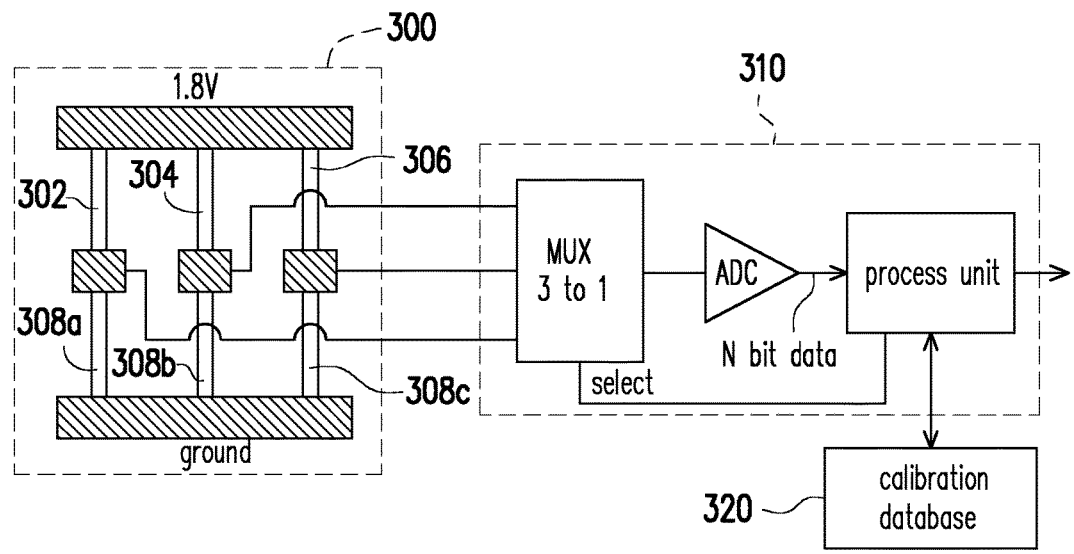
FIG. 3 is a circuit diagram of an exemplary sensor device according to a third embodiment of the disclosure.

FIG. 3 is a circuit diagram of an exemplary sensor device according to a third embodiment of the disclosure. FIG. 3 illustrates a sensor device region 300 and a reading circuit 310. The sensor device region 300 includes a humidity nanowire sensor 302, a temperature nanowire sensor 304 and a gas nanowire sensor 306, and the characteristics of these nanowire sensors can be referred to the first and second embodiments and will not reiterated herein. The reading circuit 310 in the third exemplary embodiment may concurrently read the humidity nanowire sensor 302, the temperature nanowire sensor 304 and the gas nanowire sensor 306 and convert the readouts from these sensors 302, 304, 306 to digital signal outputs. Moreover, the sensor device region 300 may also include a plurality of calibration sensors 308a-308c for calibrating the ambient conditions. The plurality of calibration sensors 308a-308c which is connected respectively with the humidity nanowire sensor 302, the temperature nanowire sensor 304 and the gas nanowire sensor 306 at one ends and is grounded at the other ends. The embodiment is exemplified by a half-bridge structure, wherein the lower half-bridge reference resistances of the humidity nanowire sensor 302 and the gas nanowire sensor 306 may directly use the resistances measured by an air-insulated temperature (nanowire) sensor, and the absolute temperature coefficient of the temperature nanowire sensor 304 is different from that of the lower half-bridge reference resistance to obtain the changes in temperature. The lower half-bridge reference resistance for the temperature nanowire sensor 304 is not attached by temperature. The voltage of the midpoint of the half-bridge is an analog voltage signal, and is converted as N bit digital data after being processed by an ADC (analog-to-digital converter) in the reading circuit 310 to facilitate the data comparison by, for example, a MCU (microcontroller) process unit.

Accordingly, when the sensors in the third exemplary embodiment start to detect, the program in the process unit of the reading circuit 310 determines which signal to select, and then switches MUX 3 to 1 (multiplexer) to obtain the midpoint voltage value of the humidity, temperature and gas nanowire sensors 302, 304 and 306 half-bridge structures. These values are respectively the responses of the humidity, temperature and gas nanowire sensors 302, 304 and 306 to the changes of humidity, temperature and gas. Then, the ADC in the reading circuit 310 converts respectively the three analog voltage values to digital values, and sends the ADC converted data to the process unit. The process unit first calculates a temperature value from the readout value of the temperature nanowire sensor 304, and then a calibration value of humidity under this temperature is extracted from the calibration database 320, for example, by implementing a look-up-table approach. After a calibrated humidity value is calculated by the process unit, a calibration value of the gas nanowire sensor 306 under the above temperature and humidity is read from the calibration database 320. The process unit again calculates a gas response value under the above temperature and humidity. The disclosure is not limited thereto. The readout circuit 310 may not use the MUX for the switching; instead, three different ADCs are correspondingly used for the conversion of the humidity, temperature and gas nanowire sensors 302, 304 and 306. Thereafter, data processing is performed by the process unit.

FIGS. 4A to 4E are schematic views exemplarily illustrating respective steps of a method for manufacturing a sensor device according to a fourth embodiment of the disclosure, wherein FIGS. 4A, 4B-1, 4C and 4D-1 are cross-sectional view, while FIGS. 4B-2, 4D-2, and 4E are perspective views.

Figure 4A:
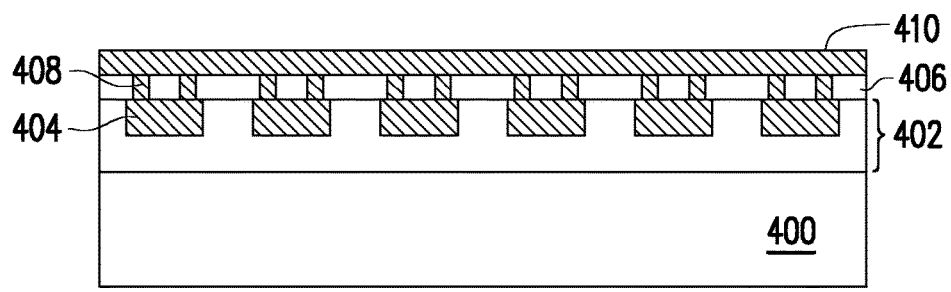

Referring to FIG. 4A, the substrate 400 includes an interconnection layer 402 thereon, and this interconnect layer 402 includes plural layers of metal conductive layers and dielectric layers (not shown), which may be connected with a transistor type of devices (not shown) disposed on the substrate 400, wherein the interconnection layer 402 is exemplified by a topmost metal layer 404 in FIG. 4A. Moreover, the insulation layer 406 formed on the interconnection layer 402 includes a plurality of contacts 408. Thereafter, a conductive layer 410 is formed, but the disclosure is not limited thereto. The interconnection layer 402 and the contacts 408 thereon in FIG. 4A may be omitted, and the conductive layer 410 is formed directly on the substrate 400.

Figures 1, 4B:
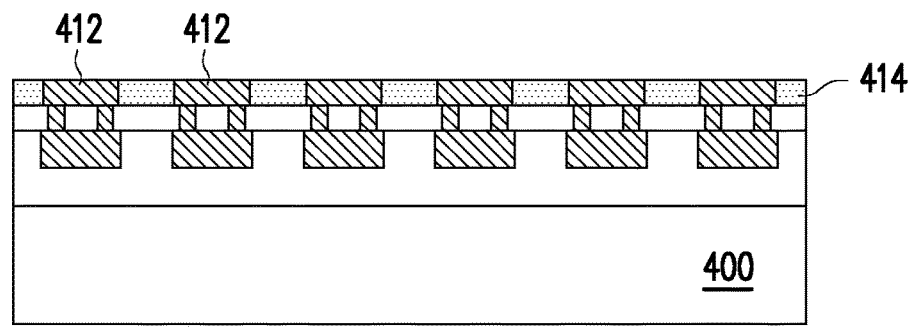
Figures 2, 4B:
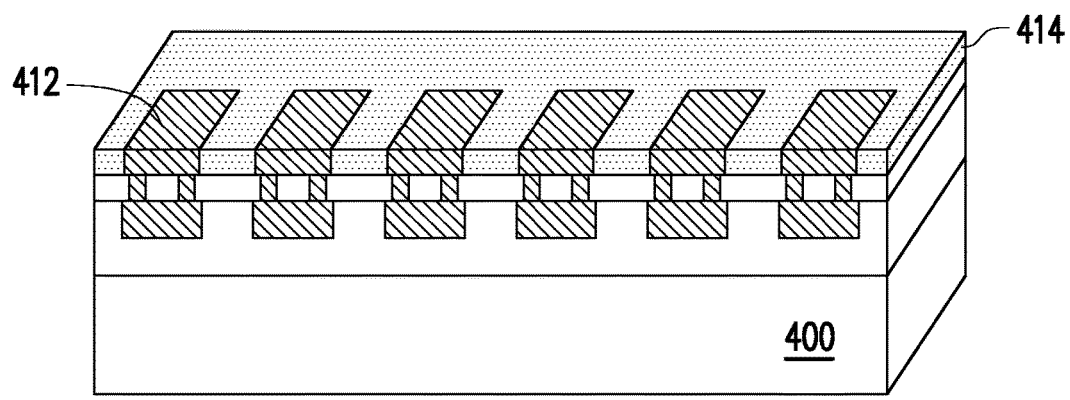

Referring to FIGS. 4B-1 and 4B-2, the conductive layer 410 of FIG. 4A is etched to from a plurality of sensing electrodes 412, and the material of the sensing electrodes 412 may be selected from at least a pure metal of or an alloy of platinum (Pt), titanium (Ti), tungsten (W), copper (Cu) and aluminum (Al), but excluding pure copper. If an alloy is used, the sensing electrodes 412 may be formed with CuAl, TiCu, TiW, TiCuAl, etc. Afterwards, an insulation layer 414 is deposited to cover the sensing electrodes 412 and fill the gaps between the sensing electrodes 412, wherein the insulation layer 414 is, for example, an oxide layer. Thereafter, a CMP (chemical mechanical polishing) process, for example, is performed to expose the sensing electrodes 412 for facilitating the subsequent nanowire process and connection.

Figure 4C:
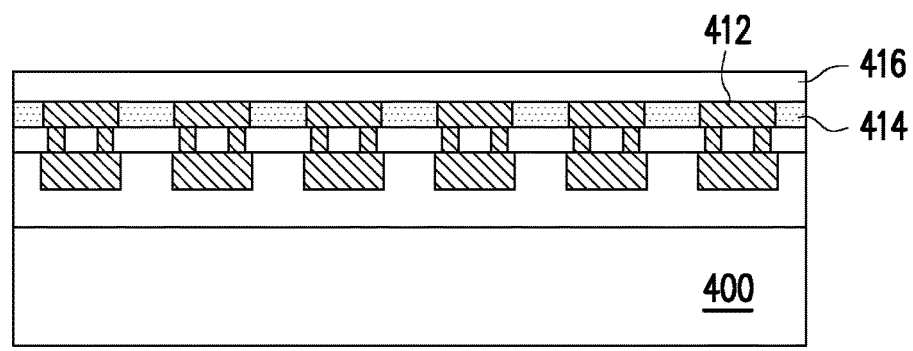

Continuing to FIG. 4C, a sensing material layer 416 is formed on the sensing electrodes 412. The material of the sensing material layer 416 is, for example, tin oxide ($SnO_2$), titanium oxide ($TiO_2$), Zinc oxide (ZnO) or polysilicon (Poly Si). The method used in forming the sensing material layer 416 includes, but is not limited to, PVD sputtering, furnace deposition, chemical bath deposition, etc.

Figures 1, 4D:
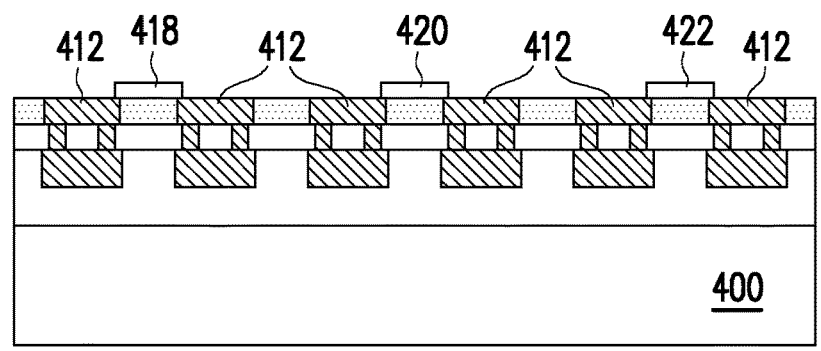
Figures 2, 4D:
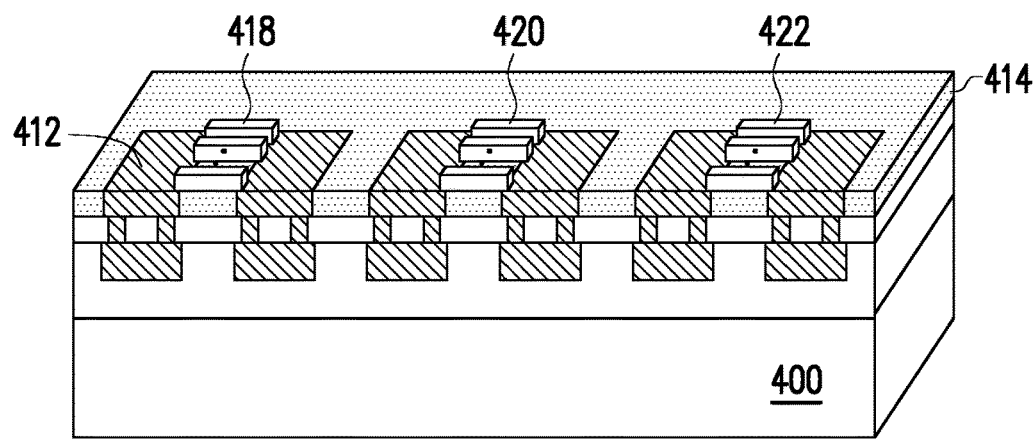

Referring to FIGS. 4D-1 and 4D-2, the sensing material layer 416 is etched to form a first nanowire sensing region 418, a second nanowire sensing region 420 and a third nanowire sensing region 422 respectively between every two sensing electrodes 412. The dimensions (diameters) of the above first, second and third nanowire sensing regions 418, 420, 422 may vary according to the design requirements, for example, ranging from 10 nm to 1000 nm, and in some embodiments, they may range from 50 nm to 350 nm. Further, the first, second and third nanowire sensing regions 418, 420, 422 may have the same or different diameters.

Figure 4E:
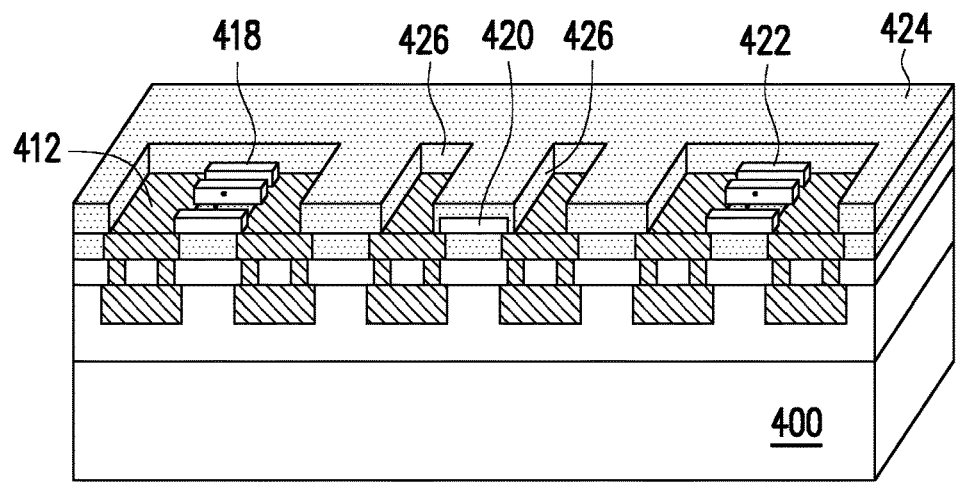

Referring to FIG. 4E, a dielectric layer 424 is formed to cover the first, second and third nanowire sensing regions 418, 420, 422. The dielectric layer 424 may be formed with, for example, silicon oxide ($SiO_2$) or silicon nitride (SiN). Thereafter, the dielectric layer 424 on the first and third nanowire sensing regions 418, 422 is removed to expose the first and third nanowire sensing regions 418, 422, which respectively serve as the humidity nanowire sensor and the gas nanowire sensor. The second nanowire sensing region 420 serving as the temperature nanowire sensor, however, is covered by the dielectric layer 424. The first nanowire sensing region 418 serving as the humidity nanowire sensor is exposed directly to air; hence, the material used in forming thereof is a hydrophilic material, such as titanium oxide, tin oxide, etc. Further, in the present embodiment, when the dielectric layer 424 on the first and third nanowire sensing regions 418 and 422 is removed, the dielectric layer on the sensing electrodes 412 may also be removed concurrently to form a plurality of pad openings 426.

FIGS. 5A-1 to 5D-2 are schematic views exemplarily illustrating variations of the fourth embodiment of the disclosure on the method for manufacturing a sensor device, wherein FIGS. 5A-1, 5B-1, 5C-1 and 5D-1 are cross-sectional views and FIGS. 5A-2, 5B-2, 5C-2 and 5D-2 are perspective views.

Figures 1, 5A:
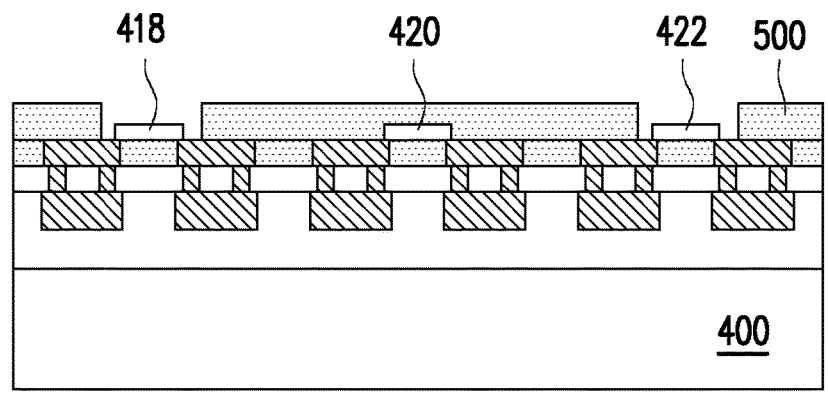
Figures 2, 5A:
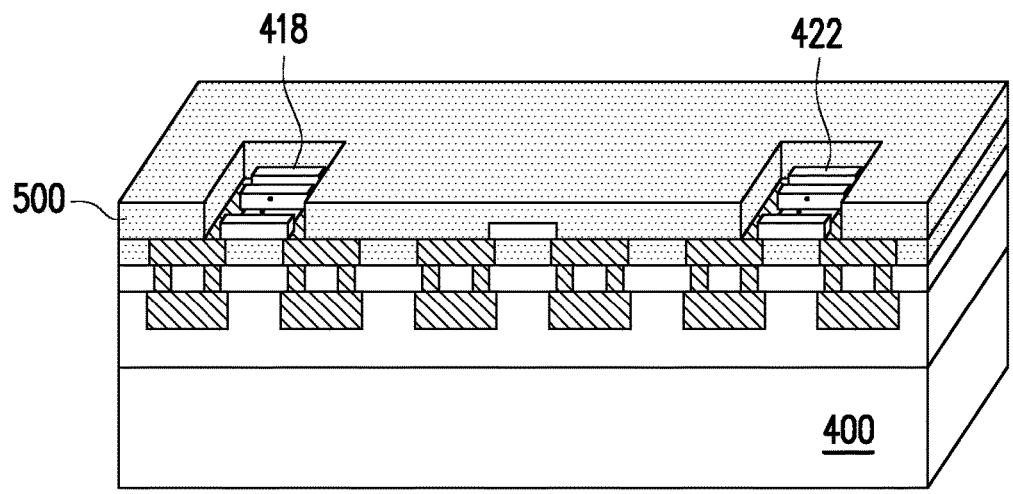

Referring to FIGS. 5A-1 and 5A-2, after the first, second and third nanowire sensing regions 418, 420, 422 are formed, continuing from FIGS. 4D-1 and 4D-2, a dielectric layer 500 is formed to cover the first, second and third nanowire sensing regions 418, 420, 422, followed by exposing the first nanowire sensing region 418 and the third sensing region 422. The above dielectric layer 500 may include silicon oxide ($SiO_2$) or silicon nitride (SiN), for example.

Figures 1, 5B:
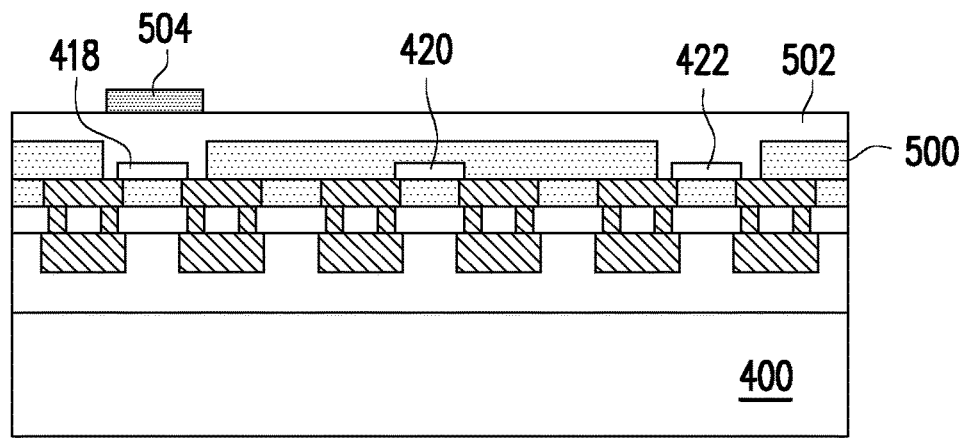
Figures 2, 5B:
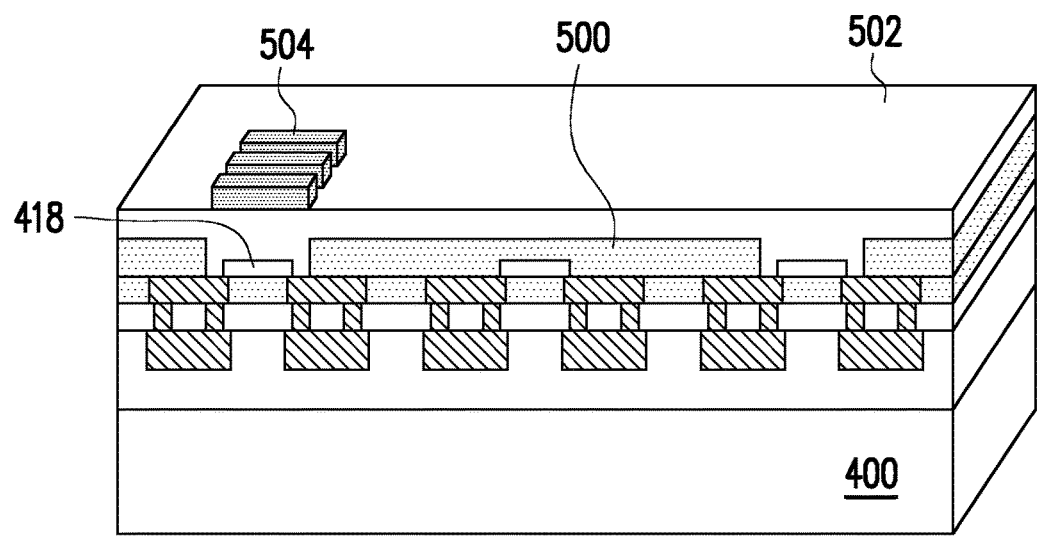

Thereafter, referring to FIGS. 5B-1 and 5B-2, a hydrophilic material layer 502 is coated on the substrate 400, wherein the hydrophilic material layer 502 may include, for example, aluminum oxide ($Al_2O_3$), titanium oxide ($TiO_2$), tin oxide ($SnO_2$), Zinc chromate ($ZnCr_2O_4$) or magnesium chromate ($MgCr_2O_4$). A photoresist 504 is further used to define the location where the hydrophilic material layer is to be retained and to facilitate the removable of the unwanted hydrophilic material. In these two Figures, the photoresist 504 is positioned above the first nanowire sensing region 418 and corresponds to the number of nanowires of the first nanowire sensing region 418, but the disclosure is not limited thereto. The position, the size and the number of the photoresist 504 may vary according to the design requirements.

Figures 1, 5C:
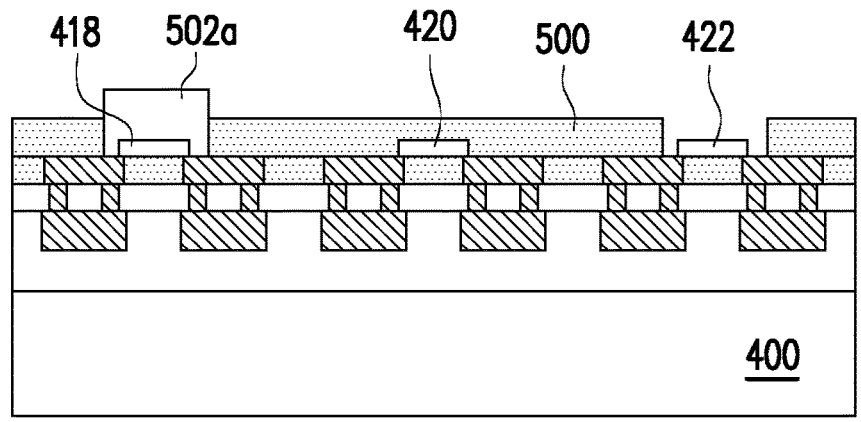
Figures 2, 5C:
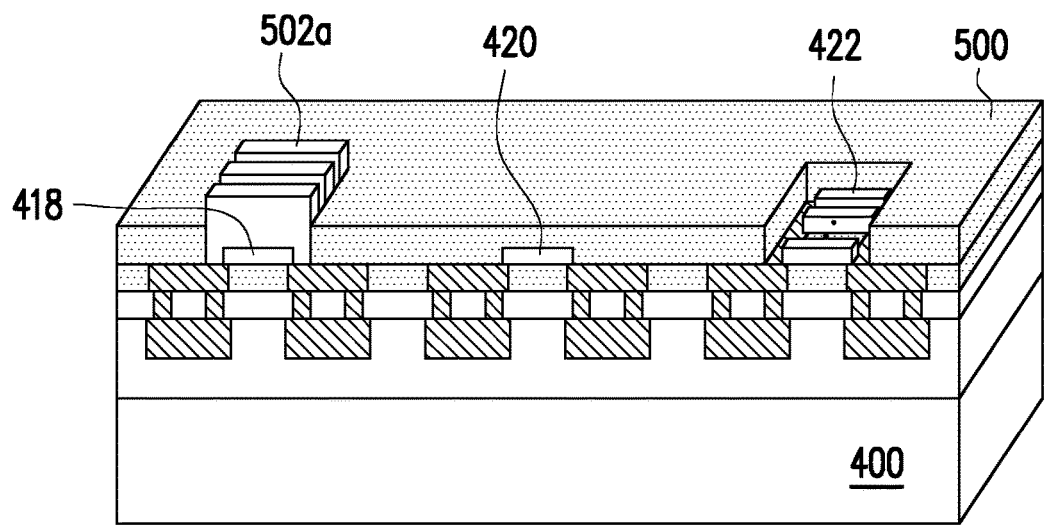

Then, continuing to FIGS. 5C-1 and 5C-2, using the photoresist 504 of FIGS. 5B-1 and 5B-2 as a shield, the exposed hydrophilic material layer 502 is removed. The hydrophilic material layer 502a is formed on the first nanowire sensing region 418, while the third nanowire sensing region 422, which serves as a gas nanowire sensor, is exposed. Ultimately, the photoresist 504 is removed.

Figures 1, 5D:
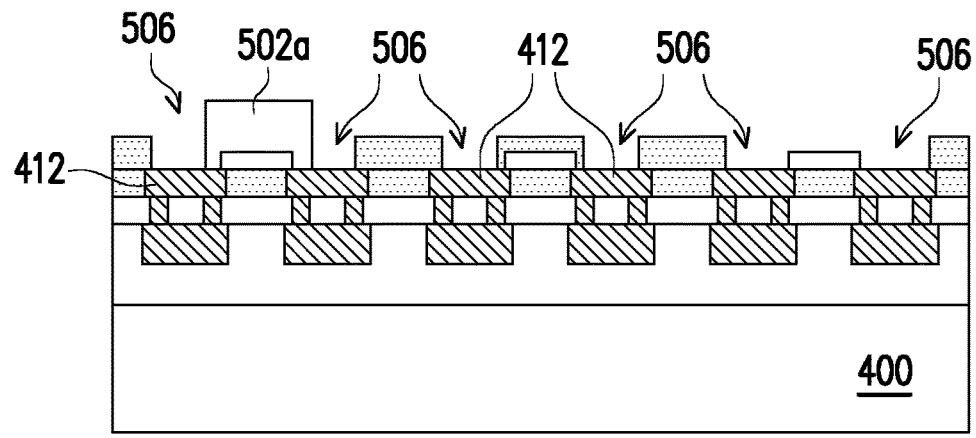
Figures 2, 5D:
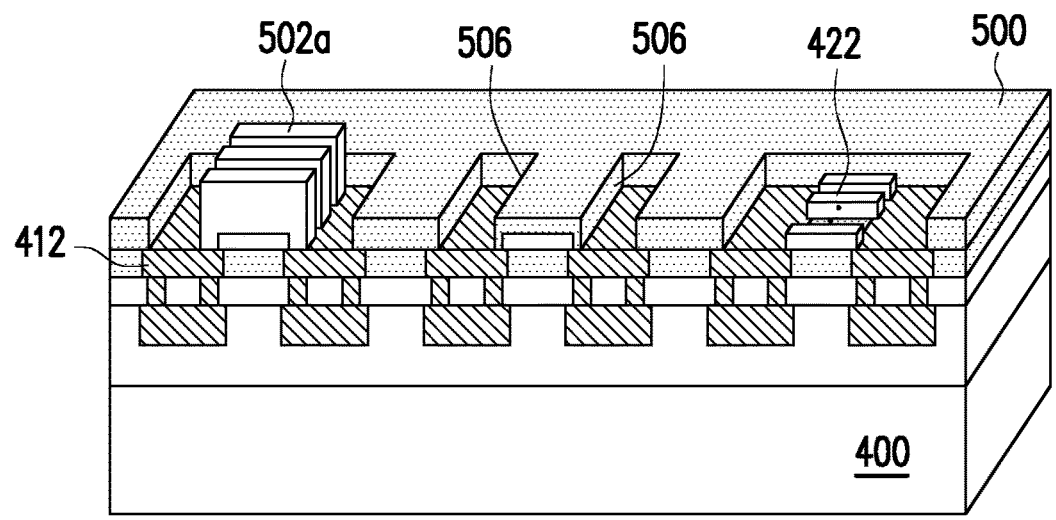

Now referring to FIGS. 5D-1 and 5D-2, the dielectric layer 500 on the sensing electrodes 412 is removed to form a plurality of pad openings 506. The exposed sensing electrodes 412 may serve as bonding pads or probe pads.

FIGS. 6A to 6E are schematic views exemplarily illustrating variations of the fourth embodiment of the disclosure on the method for manufacturing a sensor device.

Figure 6A:
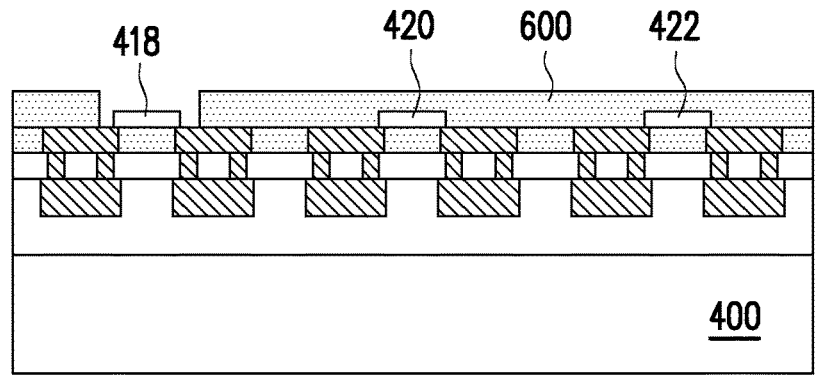
FIGS. 6A to 6E are schematic views exemplarily illustrating variations of the fourth embodiment of the disclosure on the method for manufacturing a sensor device.

Referring to FIG. 6A, after forming the first, second and third nanowire sensing regions 418, 420, 422, continuing from FIGS. 4D-1 and 4D-2, a dielectric layer 600 is formed to cover the first, second and third nanowire sensing regions 418, 420, 422, followed by exposing the first nanowire sensing region 418. The above dielectric layer 600 may be formed with silicon oxide or silicon nitride, for example.

Figure 6B:
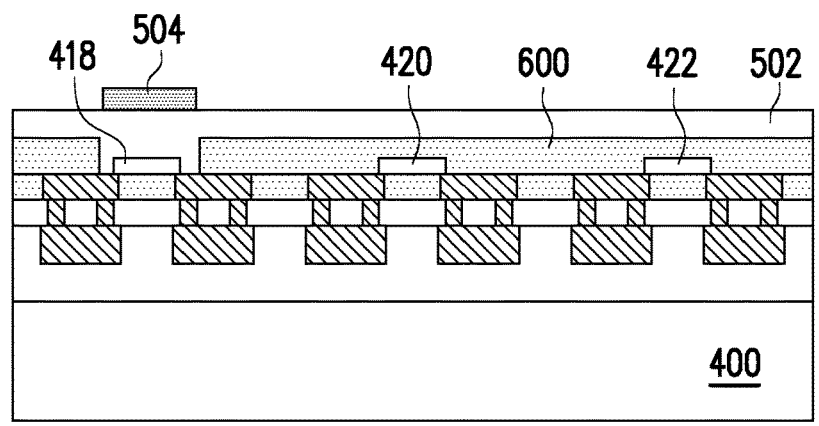

Now referring to FIG. 6B, a hydrophilic material layer 502 is coated on the substrate 400, and a photoresist 504 is used to define the location where the hydrophilic material layer is to be retained. The material of the photoresist 504 and the hydrophilic material layer 502 are similar to those described above.

Figure 6C:
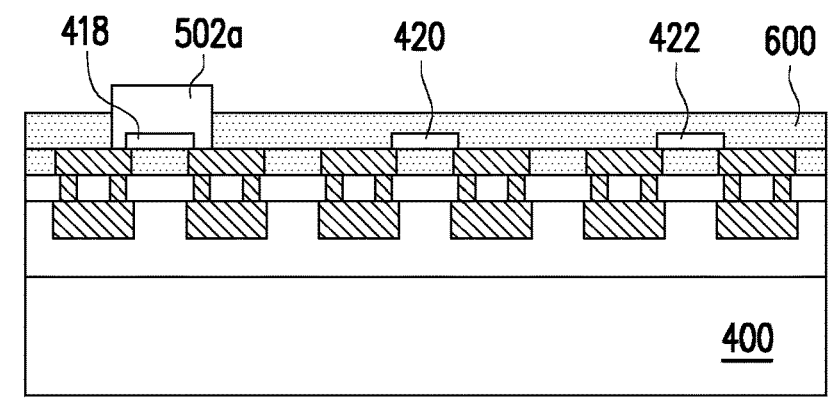

Referring to FIG. 6C, using the photoresist 504 of FIG. 6B as a mask, the exposed hydrophilic material layer 502 is removed and a hydrophilic material layer 502a is formed on the first nanowire sensing region 418. Since the third nanowire sensing region 422 which serves as a gas nanowire sensor has been covered by the dielectric layer 600, it will not be affected by the fabrication process of the hydrophilic material layer 502a. Further, no hydrophilic material residues will be remained on any part of the third nanowire sensing region 422. Ultimately, the photoresist 504 is removed.

Figure 6D:
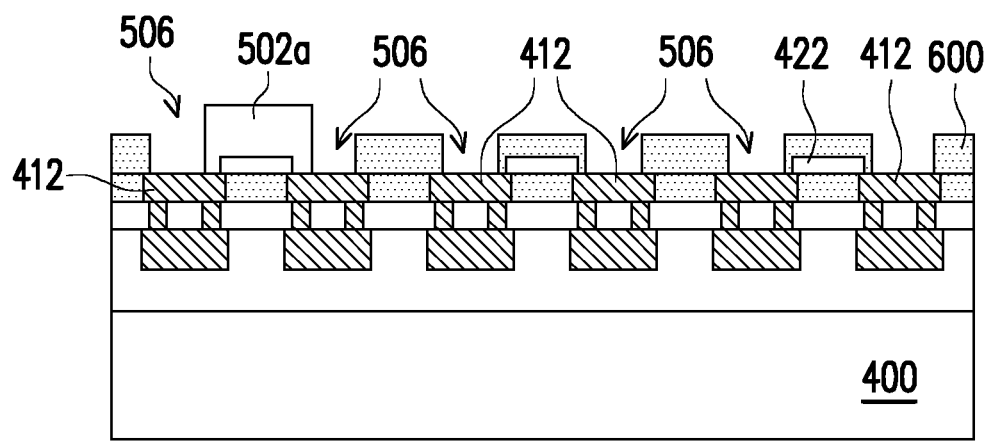

Thereafter, referring to FIG. 6D, the dielectric layer 600 on the sensing electrodes 412 is removed to form a plurality of pad openings 506.

Figure 6E:
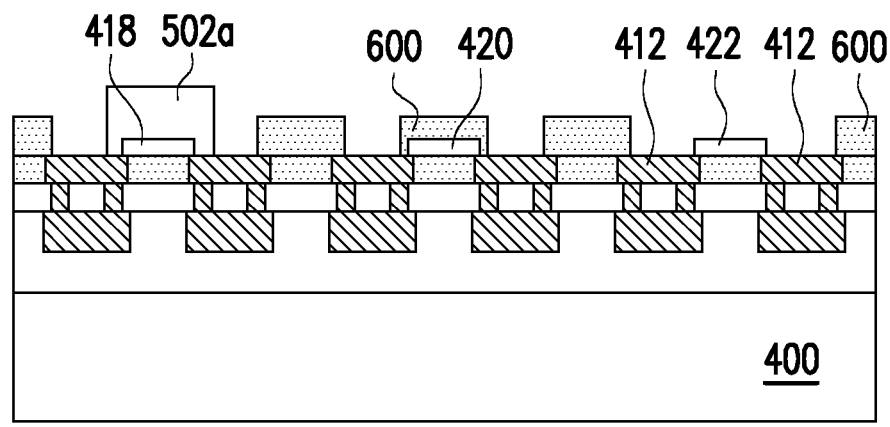

Continuing to FIG. 6E, the dielectric layer 600 on the third nanowire sensing region 422 is removed to expose the third nanowire sensing region 422 to serve as a gas nanowire sensor.

In view of the foregoing embodiments of the disclosure, the gas, temperature and humidity nanowire sensors may be concurrently fabricated to have the three sensors integrated on a same substrate. Accordingly, not only the characteristics of the nanowire sensor, such as high sensitivity, miniature, lower power consumption, etc., are provided, the overall volume can be greatly reduced to be applied to wearable devices of IoT. If a reading circuit with sufficient input range is further provided, it may read the sensors as described in the embodiments of the disclosure and then convert them into digital outputs.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A method for manufacturing a sensor device, comprising:
   forming a plurality of sensing electrodes on a substrate;
   forming a sensing material layer on the plurality of sensing electrodes;
   etching the sensing material layer to form a first nanowire sensing region, a second nanowire sensing region and a third nanowire sensing region respectively between every two sensing electrodes of the plurality of sensing electrodes;
   forming a dielectric layer to cover the first nanowire sensing region, the second nanowire sensing region and the third nanowire sensing region; and
   exposing the first nanowire sensing region and the third nanowire sensing region.

2. The method according to claim 1, wherein the step of exposing the first nanowire sensing region and the third nanowire sensing region comprises removing the dielectric layer on the first nanowire sensing region and the third nanowire sensing region to form a plurality of pad openings.

3. The method according to claim 1, further comprising forming a hydrophilic material layer on the first nanowire sensing region after the step of exposing the first nanowire sensing region and the third nanowire sensing region.

4. The method according to claim 3, wherein the hydrophilic material layer comprises aluminum oxide ($Al_2O_3$), titanium oxide ($TiO_2$), tin oxide ($SnO_2$), Zinc chromate ($ZnCr_2O_4$) or magnesium chromate ($MgCr_2O_4$).

5. The method according to claim 3, further comprising removing the dielectric layer on the plurality of sensing electrodes to form a plurality of pad openings after the step of forming the hydrophilic material layer.

6. The method according to claim 1, wherein the step of exposing the first nanowire sensing region and the third nanowire sensing region comprises:
   removing the dielectric layer on the first nanowire sensing region;
   forming a hydrophilic material layer on the first nanowire sensing region; and
   removing the dielectric layer on the plurality of sensing electrodes to form a plurality of pad openings after forming the hydrophilic material layer; and
   removing the dielectric layer on the third nanowire sensing region.

7. The method according to claim 6, wherein the hydrophilic material layer comprises aluminum oxide ($Al_2O_3$), titanium oxide ($TiO_2$), tin oxide ($SnO_2$), Zinc chromate ($ZnCr_2O_4$) or magnesium chromate ($MgCr_2O_4$).

8. The method according to claim 1, wherein the dielectric layer comprises silicon oxide ($SiO_2$) or silicon nitride (SiN).

9. The method according to claim 1, wherein a material of the plurality of sensing electrodes comprises at least one pure metal of or an alloy of platinum (Pt), titanium (Ti), tungsten (W), copper (Cu) and aluminum (Al), but excluding pure copper.

10. The method according to claim 1, wherein the sensing material layer comprises tin oxide ($SnO_2$), titanium oxide ($TiO_2$), zinc oxide (ZnO) or polysilicon (poly Si).

* * * * *